United States Patent
Griffiths (10) Patent No.: US 7,757,370 B2
(45) Date of Patent: Jul. 20, 2010

(54) METHODS OF FORMING A NEEDLE AND HUB ASSEMBLY FOR AUTOMATIC INJECTORS

(75) Inventor: Steven M. Griffiths, Ellicott City, MD (US)

(73) Assignee: Meridian Medical Technologies, Inc., Columbia, MD (US)

( * ) Notice: Subject to any disclaimer, the term of this patent is extended or adjusted under 35 U.S.C. 154(b) by 0 days.

(21) Appl. No.: 12/431,850

(22) Filed: Apr. 29, 2009

(65) Prior Publication Data

US 2009/0205744 A1 Aug. 20, 2009

Related U.S. Application Data

(60) Division of application No. 10/797,565, filed on Mar. 11, 2004, now Pat. No. 7,544,189, which is a continuation-in-part of application No. 10/690,987, filed on Oct. 23, 2003, now Pat. No. 7,621,887, which is a continuation-in-part of application No. 09/972,202, filed on Oct. 9, 2001, now Pat. No. 6,770,052, and a continuation-in-part of application No. 09/897,422, filed on Jul. 3, 2001, now Pat. No. 6,641,561.

(60) Provisional application No. 60/238,458, filed on Oct. 10, 2000, provisional application No. 60/238,447, filed on Oct. 10, 2000, provisional application No. 60/238,448, filed on Oct. 10, 2000.

(51) Int. Cl.
*B23P 11/00* (2006.01)
*B28B 5/00* (2006.01)
*A61M 5/31* (2006.01)

(52) U.S. Cl. ............... 29/525.01; 29/434; 264/251; 264/254; 264/255

(58) Field of Classification Search ........... 604/240, 604/241, 242, 243; 29/434, 525.01, 777; 264/251, 254, 255
See application file for complete search history.

(56) References Cited

U.S. PATENT DOCUMENTS

| 2,745,403 A | 5/1956 | Goldberg |
| 2,941,531 A | 6/1960 | Stevens |
| 3,063,450 A | 11/1962 | Myerson et al. |

(Continued)

FOREIGN PATENT DOCUMENTS

DE 1 691 166 7/1970

(Continued)

*Primary Examiner*—Essama Omgba
(74) *Attorney, Agent, or Firm*—Jones Day; Garry J. Tuma (57) ABSTRACT

A needle and hub assembly for automatic injectors includes a cap or skirt that has a forward surface interposed between and reinforced by first and second engaged hub portions. A needle is received in a contiguous channel formed in the two hub portions. Methods of forming the assembly include molding the first hub portion, placing the cap over the first hub portion, inserting the needle into the channel in the first hub portion, and then overmolding or otherwise forming the second hub portion on the exterior of the first hub portion and cap such that the second hub portion engages the first hub portion. An assembly created by this "two-shot" process can be used to seal a relatively large opening in a medicament cartridge and to support the needle more effectively than a conventional assembly.

20 Claims, 8 Drawing Sheets

U.S. PATENT DOCUMENTS

| | | |
|---|---|---|
| 3,406,686 A | 10/1968 | Keller |
| 3,592,245 A | 7/1971 | Schneller |
| 3,736,932 A | 6/1973 | Satchell |
| 3,757,779 A | 9/1973 | Rovinski |
| 3,863,624 A | 2/1975 | Gram |
| RE28,713 E | 2/1976 | Stevens et al. |
| 3,938,513 A | 2/1976 | Hargest |
| 3,974,832 A | 8/1976 | Kruck |
| 4,043,335 A | 8/1977 | Ishikawa |
| 4,060,082 A | 11/1977 | Lindberg et al. |
| 4,215,701 A | 8/1980 | Raitto |
| 4,266,557 A | 5/1981 | Merry |
| 4,306,554 A | 12/1981 | Schwartz et al. |
| 4,413,991 A | 11/1983 | Schmitz et al. |
| 4,529,403 A | 7/1985 | Kamstra |
| 4,568,336 A | 2/1986 | Cooper |
| 4,599,082 A | 7/1986 | Grimard |
| 4,613,326 A | 9/1986 | Szwarc |
| 4,755,169 A | 7/1988 | Sarnoff et al. |
| 4,792,329 A | 12/1988 | Schreuder |
| 4,822,340 A | 4/1989 | Kamstra |
| 4,861,335 A | 8/1989 | Reynolds |
| 4,874,381 A | 10/1989 | Vetter |
| 4,898,580 A | 2/1990 | Crowley |
| 4,983,164 A | 1/1991 | Hook et al. |
| 4,986,820 A | 1/1991 | Fischer |
| 4,994,043 A | 2/1991 | Ysebaert |
| 5,015,229 A | 5/1991 | Meyer et al. |
| 5,017,191 A | 5/1991 | Yamada et al. |
| 5,041,088 A | 8/1991 | Ritson et al. |
| 5,080,649 A | 1/1992 | Vetter |
| 5,281,198 A | 1/1994 | Haber et al. |
| 5,295,965 A | 3/1994 | Wilmot |
| 5,298,024 A | 3/1994 | Richmond |
| 5,354,286 A | 10/1994 | Mesa et al. |
| 5,364,369 A | 11/1994 | Reynolds |
| 5,391,151 A | 2/1995 | Wilmot |
| 5,397,048 A | 3/1995 | Konno et al. |
| 5,429,603 A | 7/1995 | Morris |
| 5,465,727 A | 11/1995 | Reinhold, Jr. |
| 5,472,422 A | 12/1995 | Ljungquist |
| 5,522,804 A | 6/1996 | Lynn |
| 5,569,192 A | 10/1996 | Van der Wal |
| 5,620,421 A | 4/1997 | Schmitz |
| 5,637,087 A | 6/1997 | O'Neil et al. |
| 5,704,918 A | 1/1998 | Higashikawa |
| 5,713,857 A | 2/1998 | Grimard et al. |
| 5,725,777 A | 3/1998 | Taylor |
| 5,735,825 A | 4/1998 | Stevens et al. |
| 5,785,683 A | 7/1998 | Szapiro et al. |
| 5,795,337 A | 8/1998 | Grimard |
| 5,807,344 A | 9/1998 | Iwasaki |
| RE35,986 E | 12/1998 | Ritson et al. |
| 5,865,798 A | 2/1999 | Grimard et al. |
| 5,902,277 A | 5/1999 | Jentzen |
| 5,971,953 A | 10/1999 | Bachynsky |
| 6,053,895 A | 4/2000 | Kolberg et al. |
| 6,093,172 A | 7/2000 | Funderburk et al. |
| 6,142,977 A | 11/2000 | Kolberg et al. |
| 6,149,628 A | 11/2000 | Szapiro et al. |
| 6,368,303 B1 | 4/2002 | Caizza |
| 6,379,328 B1 | 4/2002 | MacClay |
| 6,511,459 B1 | 1/2003 | Fago |
| 6,641,561 B1 | 11/2003 | Hill et al. |
| 6,656,150 B2 | 12/2003 | Hill et al. |
| 7,544,189 B2 * | 6/2009 | Griffiths .................... 604/240 |
| 2002/0049407 A1 | 4/2002 | Hill et al. |
| 2003/0040701 A1 | 2/2003 | Dalmose |

FOREIGN PATENT DOCUMENTS

| | | |
|---|---|---|
| EP | 0 112 574 | 7/1984 |
| EP | 0 361 668 | 4/1990 |
| EP | 0 405 320 | 1/1991 |
| EP | 0 511 183 | 10/1992 |
| FR | 2 245 381 | 4/1975 |
| FR | 2 604 363 | 4/1988 |
| FR | 2 741 810 | 6/1997 |
| WO | WO 94/09839 | 5/1994 |
| WO | WO 96/01135 | 1/1996 |
| WO | WO 01/93925 | 12/2001 |
| WO | WO 04/000398 | 12/2003 |

* cited by examiner

METHODS OF FORMING A NEEDLE AND HUB ASSEMBLY FOR AUTOMATIC INJECTORS

CROSS REFERENCE TO RELATED APPLICATIONS

This is a division of U.S. patent application Ser. No. 10/797,565, filed Mar. 11, 2004, now U.S. Pat. No. 7,544,189, which is a CIP of U.S. patent application Ser. No. 10/690,987 filed on Oct. 23, 2003, now U.S. Pat. No. 7,621,887, which is a CIP of U.S. patent applications Ser. No. 09/972,202, filed on Oct. 9, 2001, now U.S. Pat. No. 6,770,052, and 09/897,422, filed on Jul. 3, 2001, now U.S. Pat. No. 6,641,561, both of which claim the benefit of U.S. Provisional Application No. 60/238,458, the '422 application also claiming the benefit of U.S. Provisional Application Nos. 60/238,448 and 60/238,447, all filed on Oct. 10, 2000. The content of each is incorporated by reference herein.

FIELD OF THE INVENTION

The invention relates to drug delivery devices. More particularly, the invention relates to needle and hub assemblies for automatic injection devices.

BACKGROUND OF THE INVENTION

Many types of syringes and other injection devices are used in the medical device arts. Typical syringes, for example, use a hollow needle to deliver a medicament subcutaneously, intramuscularly, or intravenously to a patient. The needle is usually connected by a hub assembly to the portion of the syringe that holds the medicament. The hub assembly secures the needle and also supports it.

An automatic injector is a type of injection device that enables intramuscular (IM) or subcutaneous administration of a dose of medicament. In the typical automatic injector, a cartridge carries the dose of medicament and is connected to a needle assembly. The cartridge and needle assembly are contained within a housing, which also carries an actuation assembly. Activation of the actuation assembly causes the needle to penetrate and protrude from the housing and the medicament to be injected into the patient. Thus, automatic injectors allow for quick and simple IM injection of a medicament in emergency situations without the need for measuring dosages. Additionally, automatic injectors are convenient for self-administration of medicament, because the user does not see the needle before actuation of the device, and there is no need to manually force the needle into the patient.

There are three main types of automatic injectors. A first type carries its medicament mixed in liquid form. A second type of automatic injector, called a "wet/dry" automatic injector, has two separate compartments and carries its medicament in the form of two components, a dry component and a liquid component. When the actuation assembly is activated, structure within the cartridge of the automatic injector forces the dry and liquid components of the medicament to mix. A third type of automatic injector, called a "wet/wet" automatic injector, has two separate compartments and carries its medicament in the form of two liquid components. The wet/wet automatic injector includes structure within the cartridge that may force the two components to mix when the actuation assembly is activated or the automatic injector may deliver the fluid consecutively.

In one common arrangement of an automatic injector, one of the medicament compartments is directly adjacent the needle assembly. During manufacture, the compartment adjacent the needle assembly is filled with a medicament component, and the needle assembly is installed over the opening in the compartment to seal it. The needle assembly includes a needle hub and the needle itself. With this arrangement, having the opening in the cartridge and the compartment as wide as possible is beneficial, because wide openings allow for easier filling of the compartment with the medicament, especially when the medicament or component is in the form of a dry powder or a lyophilized tablet. However, the size of the opening is limited in practice because it is difficult to make a needle assembly that can seal the compartment well and support the needle adequately.

SUMMARY OF THE INVENTION

One aspect of the invention relates to a needle and hub assembly for an injection device. The needle and hub assembly comprises a cap, a first hub portion, a needle, and a second hub portion engaged with the first hub portion. The cap has an engaging portion constructed and arranged to engage an exterior surface of a cartridge and a needle-supporting portion having a wall that includes an opening therein. The wall defines interior and exterior surfaces. The first hub portion defines a needle-receiving channel through the opening in the wall and has a section that extends along the interior surface of the wall. The needle is mounted in the needle receiving channel and extends outwardly therefrom. The second hub portion is engaged with the first hub portion and receives at least a portion of the needle. The second hub portion also has reinforcing structures which extend outwardly along the exterior surface of the wall. The wall of the needle-supporting portion of the cap is reinforced on the interior surface by the first hub portion and on the exterior surface by the second hub portion.

Another aspect of the invention that relates to an automatic injector. The automatic injector comprises a housing, a cartridge, an actuation assembly, a cap, a first hub portion, a needle, and a second hub portion. The cartridge is disposed in the housing, has at least one opening, and contains a medicament. The medicament is rearwardly confined by a plunger. The actuation assembly includes a stored energy source that is capable of being released to drive the plunger through the cartridge. The cap has an engaging portion constructed and arranged to engage an exterior surface of the cartridge to cover the opening in the cartridge, and a needle-supporting portion having a wall that includes an opening therein. The wall defines interior and exterior surfaces. The first hub portion defines a needle-receiving channel through the opening in the wall and has a section that extends along the interior surface of the wall. The needle is mounted in the needle receiving channel and extends outwardly therefrom. It is adapted to expel the medicament when the plunger is driven through the chamber. The second hub portion is engaged with the first hub portion and receives at least a portion of the needle. The second hub portion also has reinforcing structures which extend outwardly along the exterior surface of the wall. The wall of the needle-supporting portion of the cap is reinforced on the interior surface by the first hub portion and on the exterior surface by the second hub portion.

Yet another aspect of the invention relates to a method of forming a needle and hub assembly. The method comprises forming a first hub portion, providing a cap having an opening therein, arranging the first hub portion such that it has a portion thereof extending through the opening in the cap, arranging a needle in a channel defined by the first hub portion, and forming a second hub portion over an exterior surface of the cap such that the second hub portion is engaged with the first hub portion and extends over at least a portion of the exterior surface of the cap.

These and other aspects, features, and advantages of the invention will become apparent from the following description.

BRIEF DESCRIPTION OF THE DRAWINGS

The invention will be described in conjunction with the following drawing figures, in which like reference numerals designate like elements throughout the figures, and in which.

DETAILED DESCRIPTION

Figure 1:
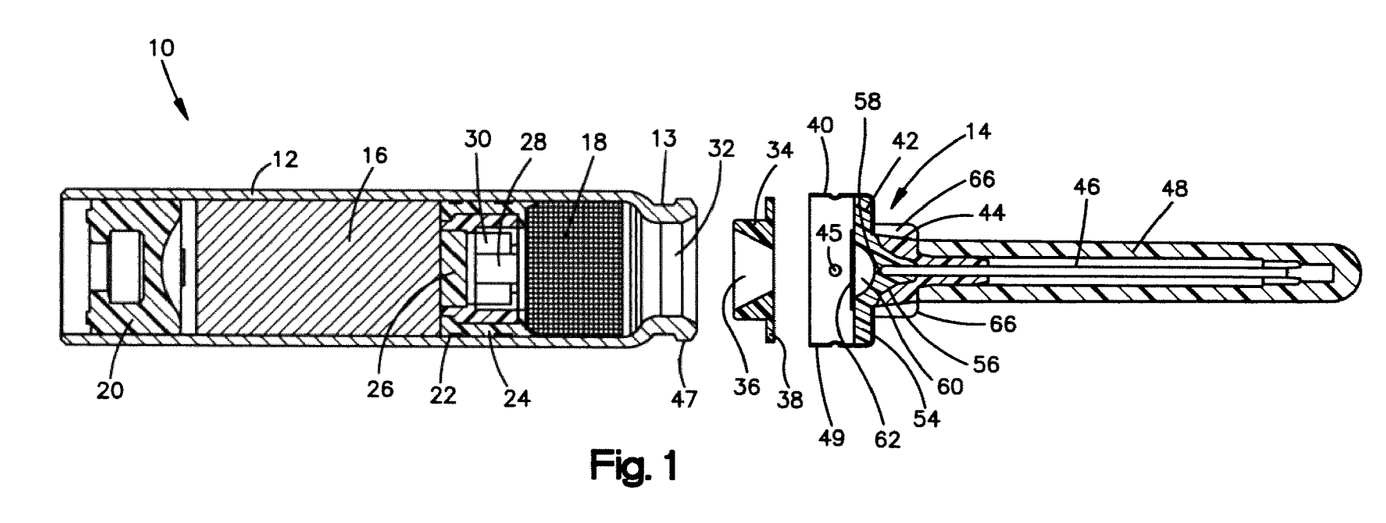
FIG. 1 is an exploded longitudinal cross-sectional view of a cartridge for an automatic injector having a needle and hub assembly according to one embodiment of the present invention.
Figure 7:
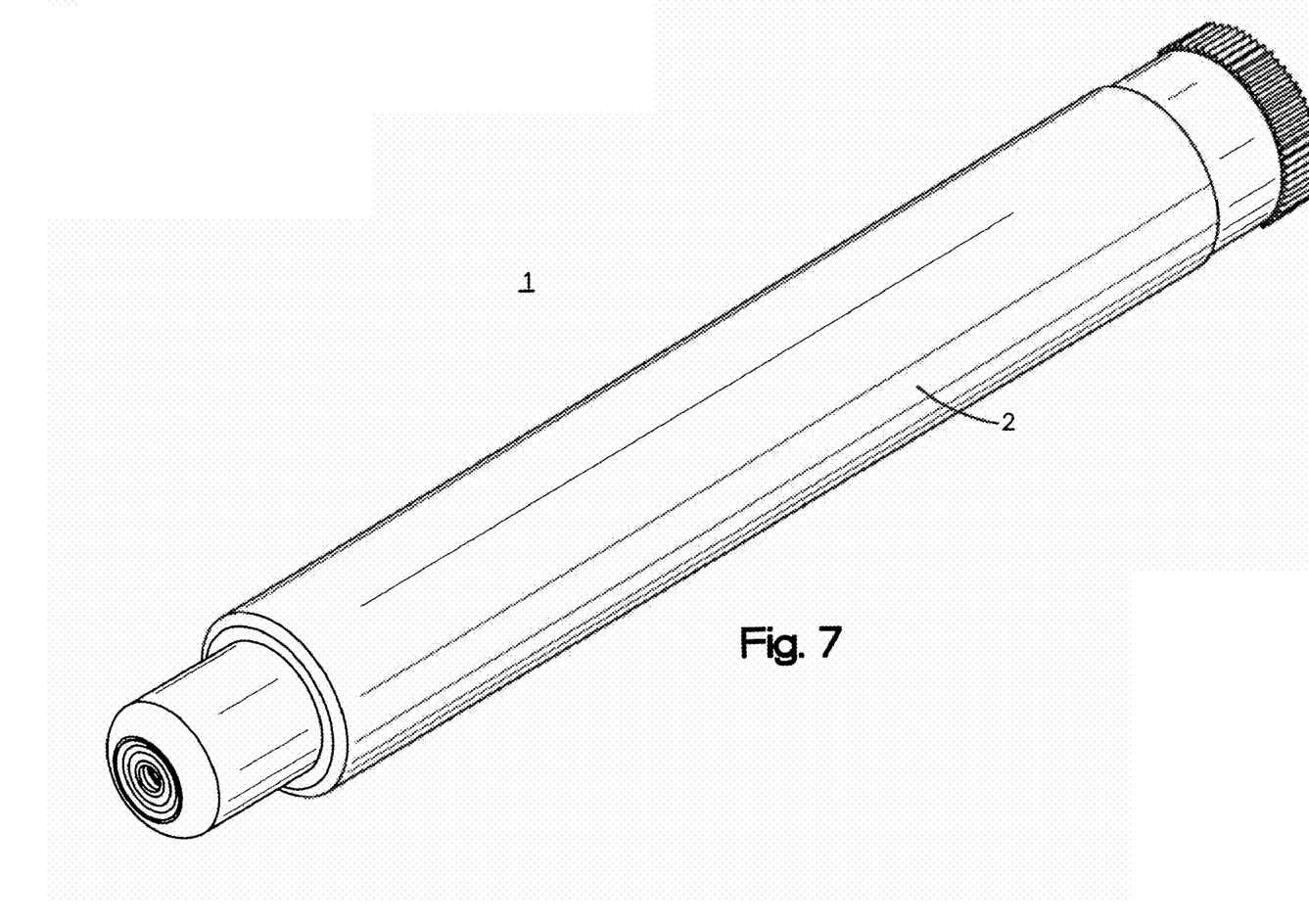
FIG. 7 is a perspective view of an autoinjector assembly having the cartridge and needle assembly according to FIG. 1.
Figure 8:
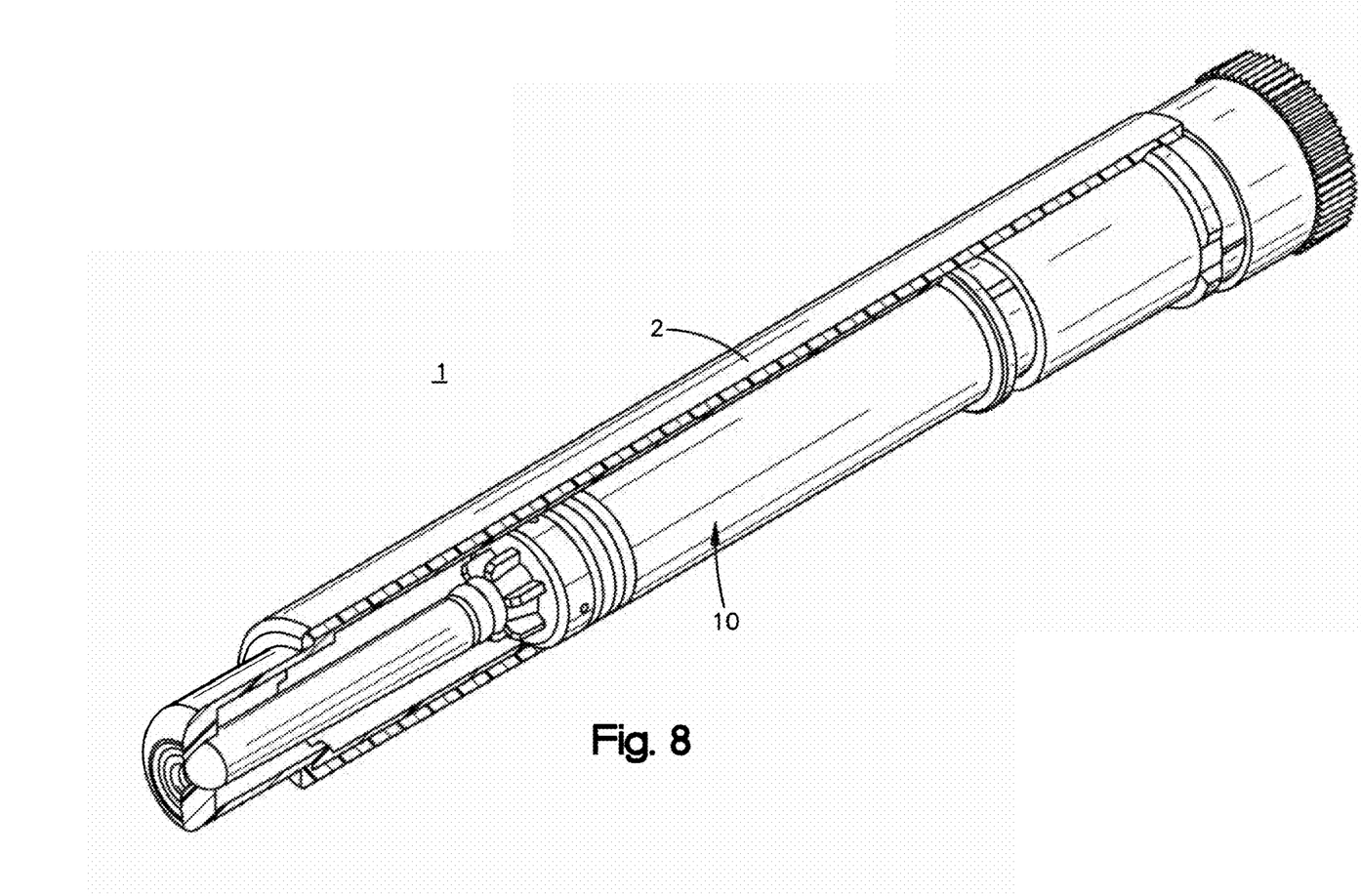
FIG. 8 is a partial cross section of FIG. 7 illustrating the cartridge and needle assembly of FIG. 1.
Figure 9:
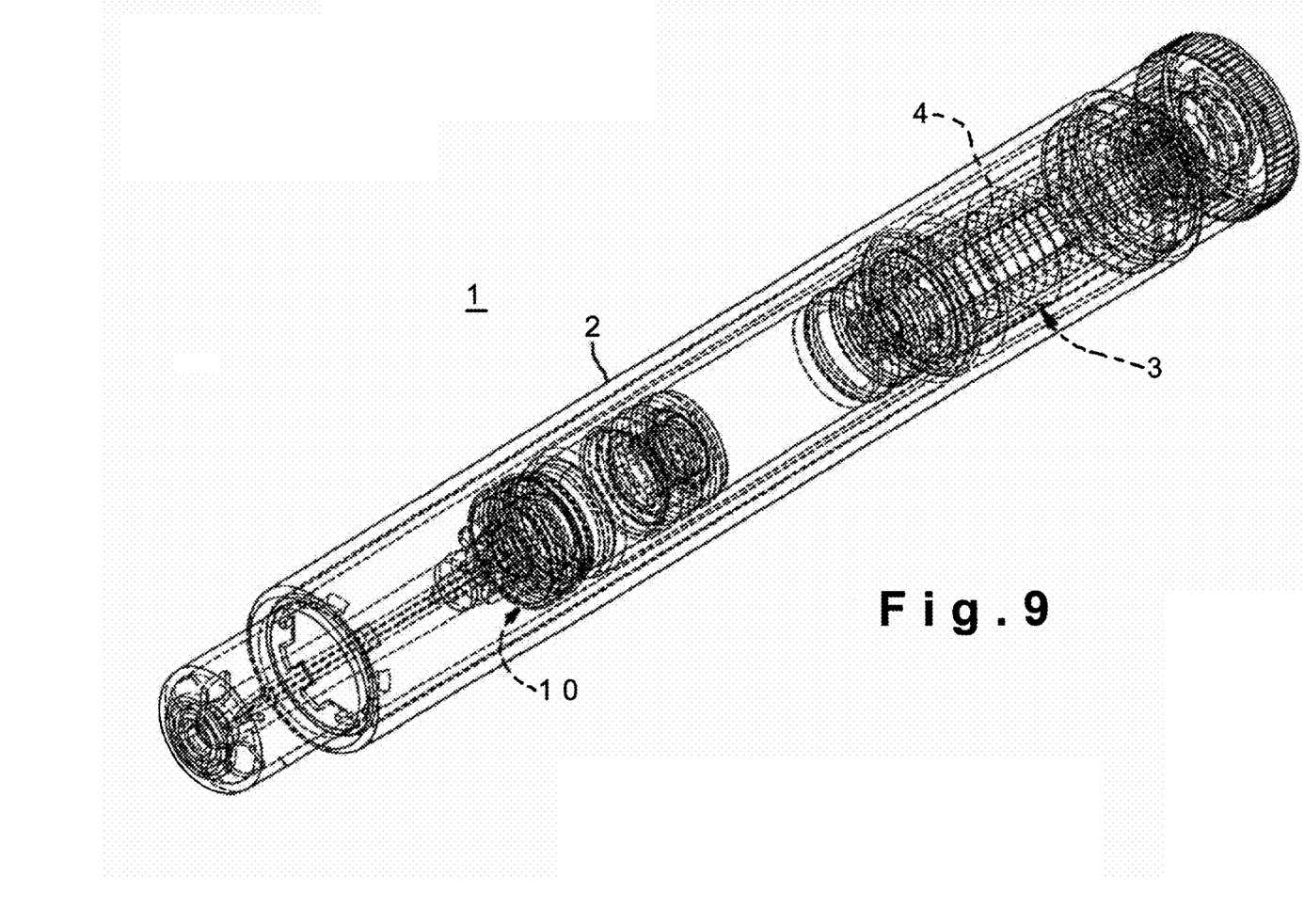
FIG. 9 is a perspective view of the autoinjector of FIG. 7 illustrating the actuation assembly.

FIG. 1 is an exploded longitudinal cross-sectional view of a cartridge and needle assembly generally indicated at 10, for an automatic injector 1, in accordance with an embodiment of the present invention. One example of the autoinjector 1 is illustrated in FIGS. 7-9. The cartridge and needle assembly 10 is generally of the type shown and described in commonly-assigned co-pending U.S. patent application Ser. No. 10/690,987, although principles, methods, and structures according to the invention are more broadly applicable to other types of cartridge and needle assemblies.

Typically, the cartridge and needle assembly 10 would be carried within an outer housing 2 that includes an actuation assembly 3 having a stored energy source 4, such as a compressed spring, shown in FIG. 9. A number of types of automatic injector housings are known in the art, and any of those types may be used with the cartridge and needle assembly 10 according to the present invention. As such, the present invention is not considered to be limited solely for use with the automatic injector illustrated in FIGS. 7-9. Furthermore, it is contemplated that the needle assembly 14 can be used in a syringe for delivering medicament.

The cartridge 12 is of the type designed to maintain a liquid medicament component separately from a dry medicament component until activation of the automatic injector, at which time the two components are mixed. However, a needle and hub assembly 14 according to embodiments of the invention may be used with a wet/dry cartridge like cartridge 12, a wet/wet cartridge, or a cartridge that is designed to house a one-component liquid medicament.

The cartridge 12 is generally formed of glass, or another rigid material that does not react with the medicament or its components. The cartridge 12 is generally cylindrical and has a smooth cylindrical inner surface. The cartridge 12 is divided into a wet medicament compartment 16 and a dry medicament compartment 18. The medicament contained within the dry medicament compartment 18 may be in powder, lyophilized, or any other solid formulation known in the art. On one end of the cartridge 12, a plunger 20 seals the liquid medicament compartment 16 and, when the actuation assembly is activated, is engaged and driven forwardly, and into the liquid medicament compartment 16. A sealing structure 22 sealingly engages the walls of the cartridge 12 to separate the liquid medicament compartment 16 from the dry medicament compartment 18.

The sealing structure 22 is of the type disclosed and claimed in commonly-assigned U.S. patent application Ser. No. 10/690,987, the disclosure of which specifically incorporated herein by reference. Although any type of sealing structure may be used, and if a wet/wet cartridge is used, the sealing structure 22 may take the form of a rupturable membrane or another more conventional type of sealing structure. The sealing structure 22 includes an outer sealing member 24, a moveable plug 26 secured within the outer sealing member 24, a flow pathway 28, and bypass zone 30. When the automatic injector is activated, the advancing plunger 20 creates a pressure in the liquid medicament compartment 16, which causes the moveable sealing plug 26 to move forwardly within the sealing structure 22. Once the sealing plug 26 has moved forwardly within the sealing structure 22, the fluid in the liquid medicament compartment 16 can enter the bypass zone 30 and mix with the medicament component in the dry medicament compartment 18.

Methods of filling the cartridges of automatic injectors such as cartridge 12 are described in U.S. patent application Ser. No. 10/690,987, and will not be repeated here in great detail. Briefly, one difficulty with traditional filling methods is that in a two-compartment cartridge, such as cartridge 12, if both medicament components are filled through the same opening, cross-contamination may easily occur. That is, a powder component may inadvertently be mixed with a liquid component or vice versa, especially around the opening. Therefore, especially with two-compartment cartridges, it is advantageous if the two components are filled through separate openings in the cartridge 12. As was noted above, it is also beneficial if the openings are relatively wide. In addition to allowing easier and faster filling of both wet and powder medicament components, wide openings allow a dry medicament tablet that has been lyophilized in a separate container to be placed directly in the dry medicament compartment 18. In the cartridge 12, the dry medicament compartment 18 has a relatively wide opening 32 located in the forward end of the cartridge 12, adjacent the needle and hub assembly 14.

In one filling process according to the invention, once the dry component is loaded into the dry medicament compartment 18, an insert 34 is inserted into the opening 32. The insert 34 has a tapering flow pathway 36 and acts to funnel the mixed medicament components toward the needle and hub assembly 14 (i.e., forwardly and inwardly) when the automatic injector is activated. The tapered insert 34 also includes a flange portion 38 that forms a seal between the opening 32 and the needle and hub assembly 14. In other filling processes, a needle and hub assembly may be directly sealed over the opening 32 without an insert or other directing structure within the cartridge 12. The diameter of opening 32 may range from 0.280" to 0.500".

Traditionally, a needle and hub assembly for this type of cartridge would be formed by staking a needle in an aluminum hub. Generally, a 20 to 24 gauge stainless steel needle would be staked into a 0.010" to 0.015 thick aluminum extruded shell, which opens to cover an opening in the cartridge having an outside diameter of 0.25" to 0.30". In the case of an opening as wide as the opening 32 (e.g., 0.472"), it is difficult to make a traditional extruded aluminum hub that can hold the needle securely and attach it to the cartridge 12. In order to solve this problem, the needle and hub assembly 14 of the present invention includes both traditional extruded components and injection molded components, and is preferably made by a multi-step injection molding process, as will be explained below.

Specifically, the hub and needle assembly 14 comprises a rigid cap or skirt 40, which may be formed of a metal, a first molded hub portion 42, a second molded hub portion 44, a needle 46, and a needle sheath 48. If the skirt 40 is formed of a metal, it would typically be extruded, although it could also be cast or otherwise formed. Although the first and second molded hub portions 42, 44 are described separately in some of the paragraphs below so as to facilitate description, they are preferably fused together during manufacture and function as a single component, as will be explained. Additionally, although the skirt 40 is described as being formed of a metal, it may also be formed of a plastic material having sufficient rigidity.

Figure 2:
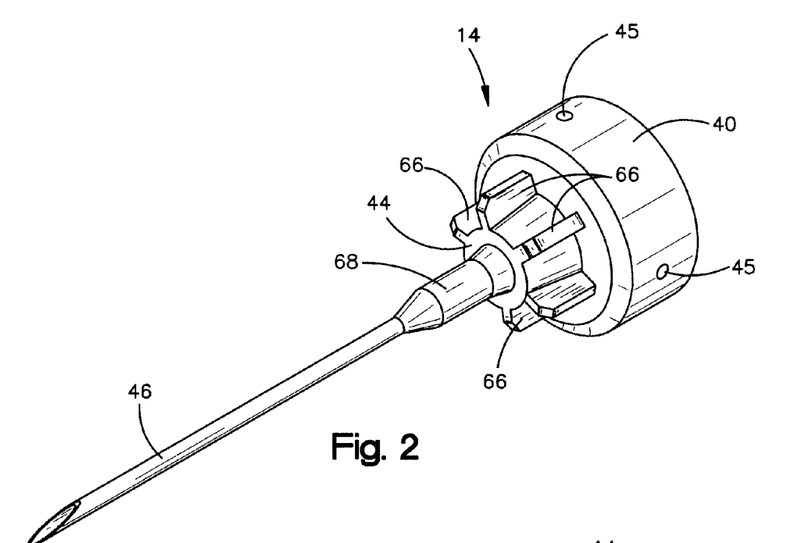
FIG. 2 is a perspective view of the hub assembly of FIG. 1 in isolation.
Figure 3:
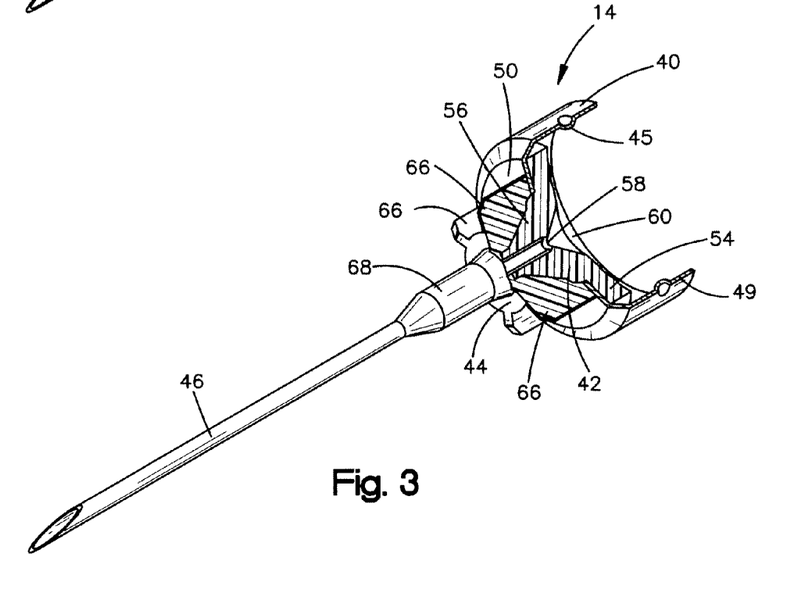
FIG. 3 is a partially sectional perspective view of the needle and hub assembly of FIG. 1.
Figure 4:
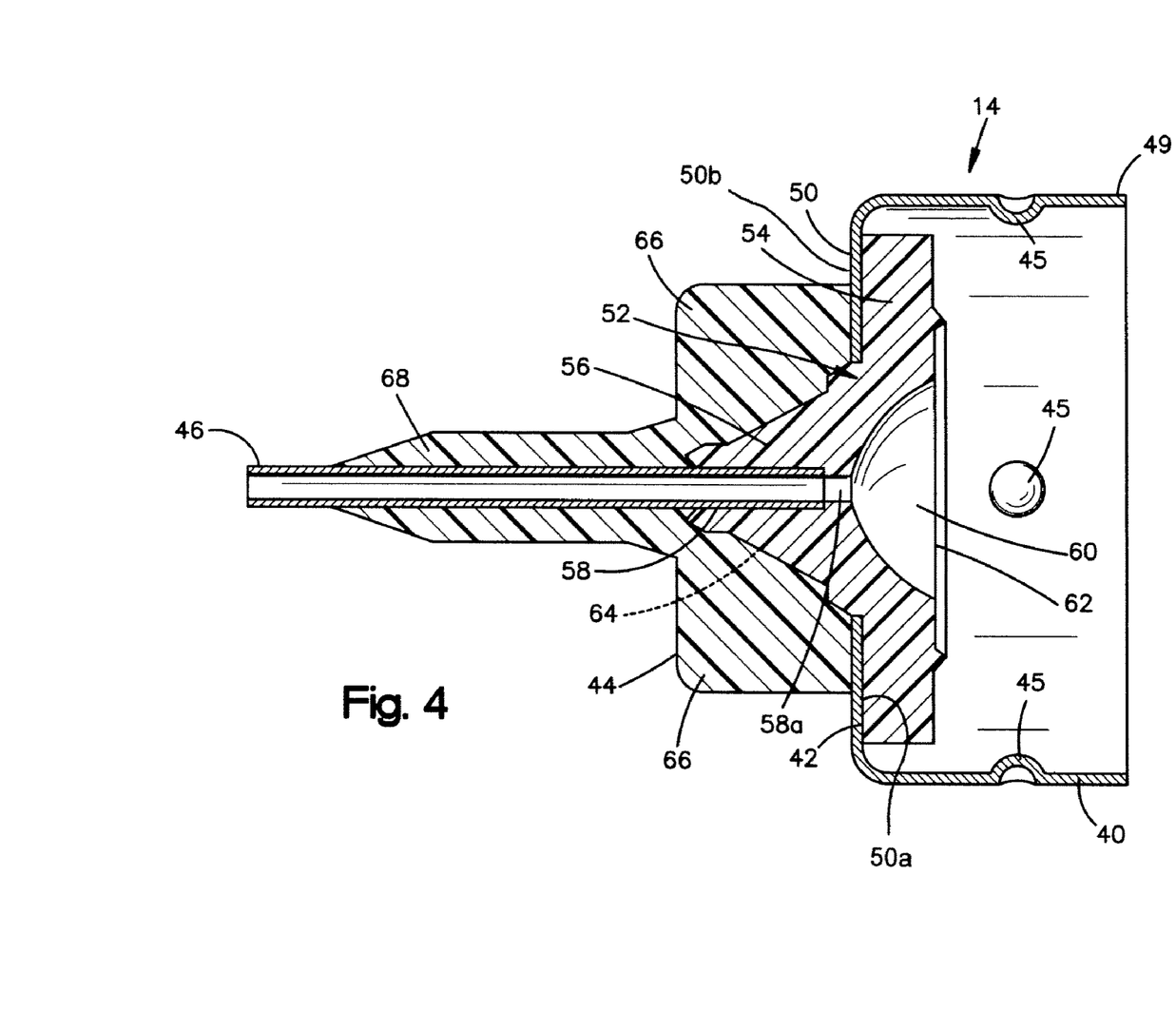
FIG. 4 is a longitudinal cross-sectional view of the needle and hub assembly of FIG. 1.

The components of the needle and hub assembly 14 can be more clearly seen in FIG. 4, which is a longitudinal cross-sectional view of the components of the needle and hub assembly 14 in isolation, as well as in FIGS. 2 and 3, which are a perspective view and a partially sectional perspective view, respectively, of the needle and hub assembly 14.

As is shown in the views of FIGS. 3 and 4, the skirt 40 is a generally cylindrically-shaped component of sufficient diameter to fit over the outside of the cartridge 12 so as to close the opening 32 in the dry compartment 18. The skirt 40 has one or more hemispherical interior protrusions 45 that are designed to be press fit onto the surface 47, shown in FIG. 1 The lower portion 49 of the skirt 40 is rolled or press fit into the groove 13 in the cartridge 12 in order to secure the needle and hub assembly 14 to the cartridge 12. The needle-supporting end or portion 50 of the skirt 40, which is opposite the end or portion of the skirt 40 that engages the cartridge 12, comprises a wall that is closed except for a central hole 52. As can be seen most clearly in FIG. 4, the needle-supporting end 50 of the skirt 40 is essentially "sandwiched" between the first and second molded hub portions 42, 44. That positioning of the needle-supporting end 50 of the skirt 40 between the first and second molded hub portions 42, 44 is mutually reinforcing and adds to the rigidity of the overall structure.

The first molded hub portion 42 is positioned along the interior surface 50a of the needle-supporting end 50 of the skirt 40 such that a flange portion 54 of the first molded hub portion 42 is adjacent to the needle-supporting end 50 of the skirt 40 and a forward portion 56 of the first molded hub portion extends through hole 52 in the needle-supporting end 50 of the skirt 40. The needle 46 is mounted within a central channel 58 of the first molded hub portion 42 just beyond the hole 52 in the skirt 40. The needle 46 extends to a stop 58a, shown in FIG. 4, formed in the channel 58 such that the needle can be reliably inserted to the same depth during manufacture. The stop 58a limits the insertion depth of the needle 46 within the first molded hub portion 42. Only a short length of the needle 46 is held within the first molded hub portion 42.

As can be seen in FIGS. 3 and 4, the first molded hub portion 42 of the illustrated embodiment defines a chamber 60 which is substantially hemispherical in shape. The channel 58 supporting the needle 46 opens into the chamber 60. A filter 62 covers the wide opening of the chamber 60. The chamber 60 and filter 62 are provided to direct the flow from the cartridge 12 toward the needle 46 and to allow for more fully-developed flow "behind" the filter 62. The particular features and advantages of these components were described in co-pending U.S. application Ser. No. 10/690,987, of which this application is a continuation-in-part.

It should be understood that the chamber 60 and filter 62 are optional components and need not be included in embodiments of the invention. Moreover, as will be readily understood by those skilled in the art, the first molded hub portion 42 may include whatever contours or structural features are necessitated by the interior arrangement of the automatic injector with which it is designed to be used. In general, the structural features of the first molded hub portion 42 inside of the skirt 40 are not critical to the invention, provided that the first molded hub portion 42 includes structures of sufficient extent to retain it in position within the skirt 40 and to reinforce the skirt 40.

The second molded hub portion 44 is disposed on the outside of the needle-supporting end 50 of the skirt 40. It abuts the exterior surface 50b of the needle-supporting end 50 and creates a meltzone 64 where the pieces 42 and 44 are permanently joined. During formation of hub portion 44, the first molded hub portion 42 is remelted so that the portions 42 and 44 are joined together. As can be seen most clearly in FIGS. 2 and 3, the second molded hub portion 44 includes a number of radially extending ribs 66 which abut the exterior surface 50b of the needle-supporting end 50 and extend outwardly across it. The ribs 66 act to stabilize and reinforce the needle-supporting end 50 of the skirt 40 and prevent it from warping, distorting, or otherwise deforming due to the stresses encountered during automatic injection. Contiguous with the ribs 66 is a forwardly-extending tapering portion 68 which supports the needle 46 along a greater portion of its length. Because of the first and second molded hub portions 42, 44, the needle-supporting end 50 of the skirt 40 is reinforced and the needle 46 itself is well supported.

The needle assembly 14 according to the present invention is most advantageously manufactured using a several step injection-molding process. The first and second molded hub portions 42, 44 may be made of ABS, polyethylene, polypropylene, or another well known medical grade polymer. The injection molding process for the needle assembly 14 will be explained below with respect to FIGS. 5A-5D, which are perspective views of the needle assembly 14 at various stages of manufacture, and FIG. 6, a high-level block diagram of the steps involved in the process. Suitable injection molding apparatus for these processes is well known in the art. One example of an appropriate injection molding apparatus that may be used in a process according to the invention is the Arburg Model 270 All Rounder.

Figure 5A:
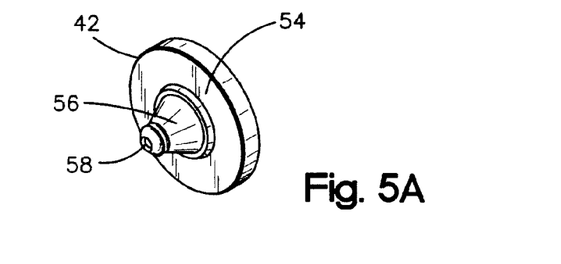
FIGS. 5A-5D are perspective views of the need and hub assembly of FIG. 1 after each successive step of manufacture.
Figures 5B, 5C, 5D:
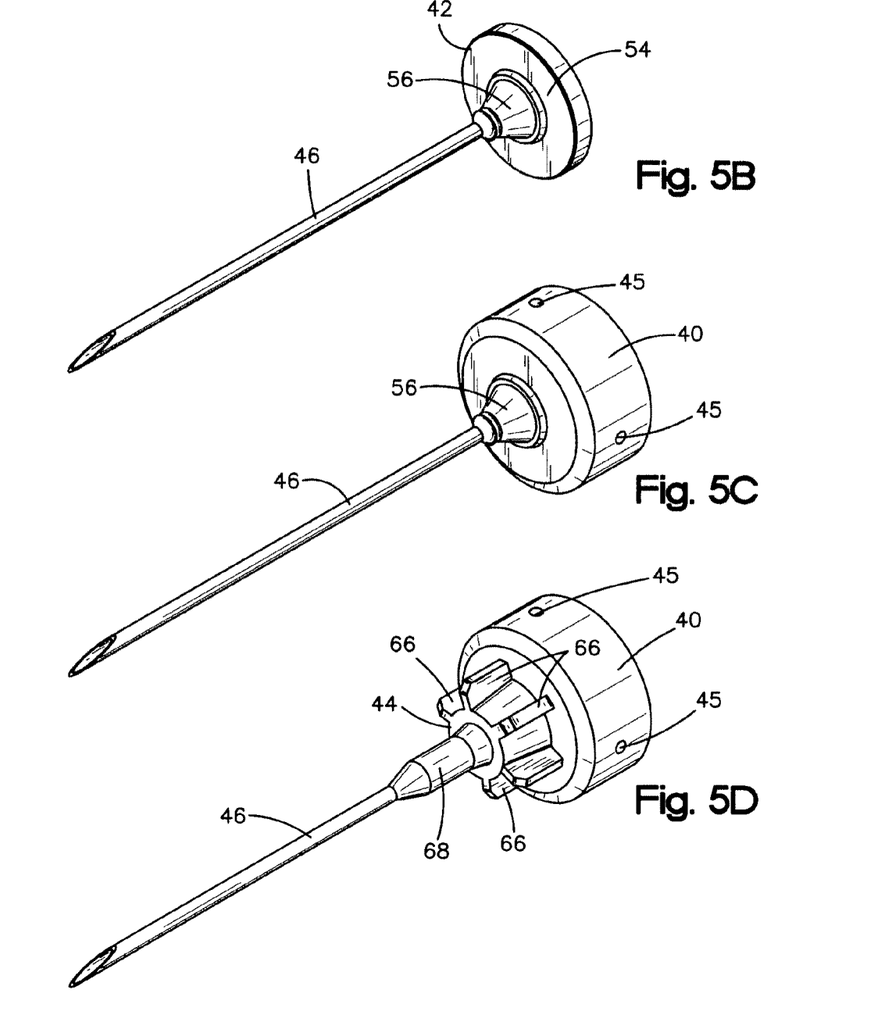
Figure 6:
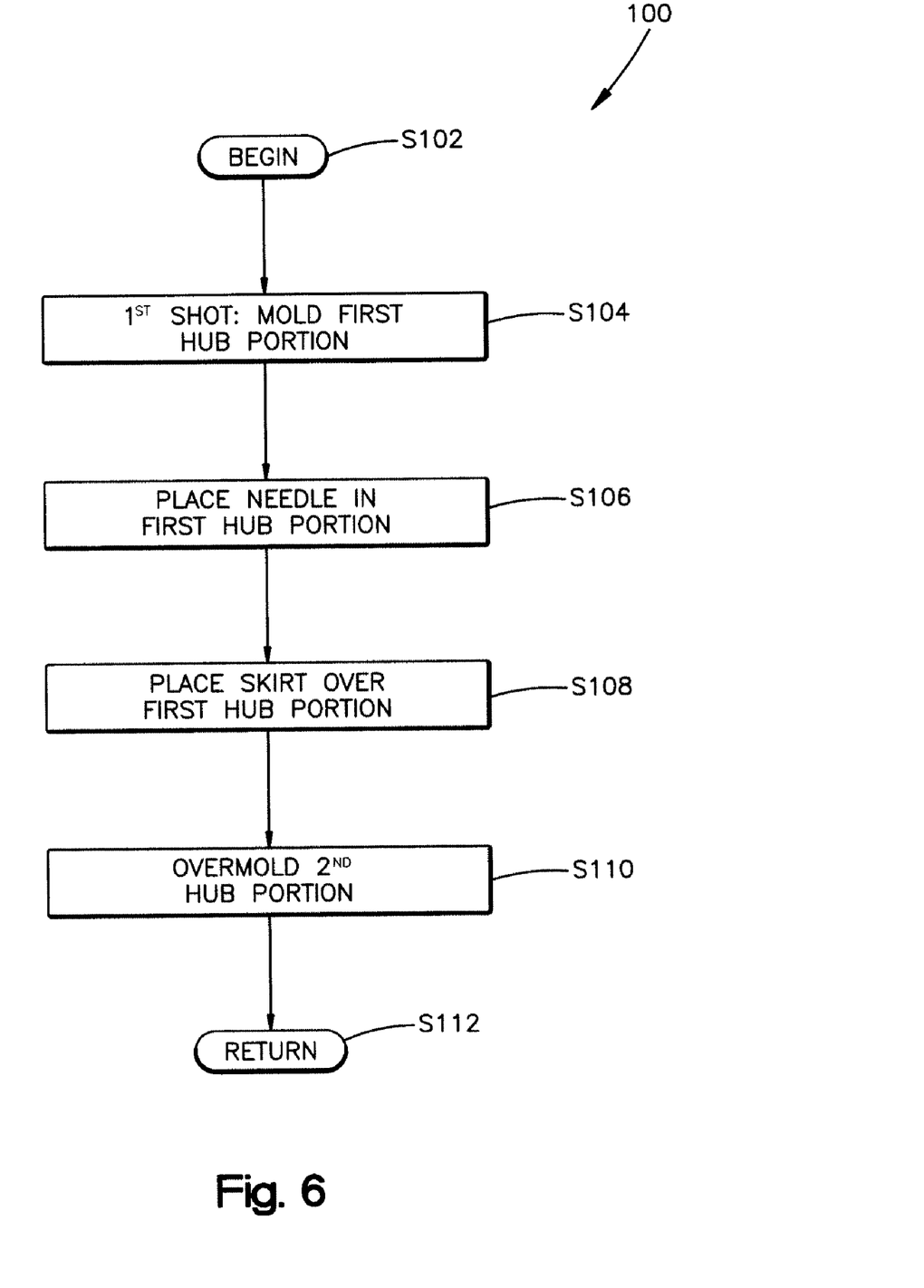
FIG. 6 is a high level schematic block diagram of a process for manufacturing a needle and hub assembly according to the invention.

Manufacturing process 100 for the needle and hub assembly 14 begins at S102. Before the actual molding process begins, the user would prepare the equipment and provide appropriate mold parts for the components. The process continues at S104. At S104, the user injects heated fluid plastic material into a mold component having a cavity that defines the shape of the first molded hub portion 42. The fluid plastic cools within the mold cavity to become the first molded hub portion 42, as shown in FIG. 5A. The hub portion 42 is then ejected from the mold. The process 100 continues at S106. At S106, a needle 46 is placed in the channel 58 in the first molded hub portion 42, as shown in FIG. 5B until the needle 46 contacts stop 58a. Once the needle 46 is placed in the channel 58, process 100 continues with S108, in which an extruded metal skirt 40 is placed over the exterior of the first molded hub portion 42. Once the skirt 40 and needle 46 are in place, the assembly, which is shown in FIG. 5C, is removed from the first mold and placed in the second mold. Cavities in the second mold define the shape of the second molded hub portion. Once the assembly is in place, process 100 continues with S110, in which the second molded hub portion 44 is overmolded onto the assembly, forming the completed needle and hub assembly 14 shown in perspective in FIG. 5D. As discussed above, during the molding of the hub portion 44, a portion of the surface area of the hub portion 42 is remelted to form a melt zone 64 such that the portions 42 and 44 are fused together to form a single piece. The process 100 ends at S112 and may be repeated as many times as is desired.

When the second molded hub portion 44 is overmolded in S110 of process 100, the second molded hub portion 44 fuses with the first molded hub portion 42 along melt zone 64 as it cools, forming an integral, fused component. For this reason, it is typically advantageous to mold the first and second molded hub portions 42, 44 of the same material so that they can fuse together effectively. However, any two thermally compatible materials may be used for the first and second molded hub portions 42, 44.

Process 100 also provides certain other advantages over more conventional methods of manufacturing a needle and hub assembly. For example, although the components illustrated in the Figures could be molded separately, assembled, and bonded, welded, or fit together, process 100 provides much tighter tolerances than would exist if any of those more conventional processes were used.

Although the invention has been described with respect to certain embodiments, those embodiments are intended to be exemplary only, and should not be construed as limiting. Modifications and variations to the invention as described herein may be made within the scope of the appended claims.

I claim:

1. A method of forming a needle and hub assembly for automatic injectors, the method comprising:
    forming a first hub portion having a forward section and a flange section, the forward section defining a needle-receiving channel;
    inserting a needle in the needle-receiving channel;
    forming a cap having an engaging portion and a needle supporting portion, the engaging portion configured to engage a medicament cartridge of an automatic injector, the needle-supporting portion having a wall that includes an opening therein, the wall defining interior and exterior surfaces opposite each other;
    arranging the cap over the needle and the first hub portion such that:
        the needle and the forward section of the first hub portion extend through the opening in the wall of the cap, and
        the flange section of the first hub portion extends along and abuts the interior surface of the wall of the cap; and
    forming a second hub portion over the needle and first hub portion, the second hub portion having a forward tapering section and a plurality of radially-extending structures, the forward tapering section defining a needle-receiving channel in alignment with the needle-receiving channel of the first hub portion, the forward tapering section of the second hub portion engaging the forward section of the first hub portion, and the radially-extending structures abutting the exterior surface of the wall of the cap and extending outwardly across the wall to form a contiguous structure of the second hub portion that extends along the interior and exterior surfaces of the wall, the wall, and the first hub portion.

2. A method of assembling an automatic injector comprising:
    providing an outer housing of the automatic injector;
    providing an actuation assembly in the outer housing;
    filling a medicament cartridge with one or more medicament components, the medicament cartridge having an open end;
    attaching the needle and hub assembly formed by the method of claim 1 over the open end of the medicament cartridge; and
    inserting the medicament cartridge with attached needle and hub assembly in the outer housing, the medicament cartridge in communication with the actuation assembly.

3. The method of claim 1 wherein forming the cap comprises extruding a metal to form the cap.

4. The method of claim 1 wherein forming the cap having an engaging portion comprises forming a cylindrically-shaped cap of sufficient diameter to fit over the outside end of a medicament cartridge.

5. The method of claim 1 wherein forming the cap having an engaging portion comprises forming hemispherical interior protrusions on the engaging portion configured to be press fit over a corresponding groove on an exterior surface of a medicament cartridge.

6. The method of claim 1 wherein forming the first hub portion and the second hub portion comprises injection molding the first and second hub portions.

7. The method of claim 1 wherein forming the first hub portion and the second hub portion comprises forming the first and second hub portions with a medical grade polymer.

8. The method of claim 1 wherein forming the first hub portion and the second hub portion comprises forming the first and second hub portions with thermally compatible materials.

9. The method of claim 1 wherein forming the second hub portion comprises overmolding the second hub portion onto the needle and first hub portion.

10. The method of claim 1 wherein forming the second hub portion comprises permanently joining the forward tapering section of the second hub portion to the forward section of the first hub portion.

11. A method of forming a needle and hub assembly for automatic injectors, the method comprising:
    forming a first hub portion having a forward section and a flange section, the forward section defining a needle-receiving channel;
    inserting a needle in the needle-receiving channel;
    forming a cap having an engaging portion and a needle supporting portion, the engaging portion configured to engage a medicament cartridge of an automatic injector, the needle-supporting portion having a wall that includes an opening therein, the wall defining interior and exterior surfaces opposite each other;
    arranging the cap over the needle and the first hub portion such that:
        the needle and the forward section of the first hub portion extend through the opening in the wall of the cap, and
        the flange section of the first hub portion extends along and abuts the interior surface of the wall of the cap; and
    forming a second hub portion over the needle and first hub portion, the second hub portion having a forward tapering section and a plurality of radially-extending structures, the forward tapering section defining a needle-receiving channel in alignment with the needle-receiving channel of the first hub portion, the forward tapering section of the second hub portion engaging the forward section of the first hub portion causing a portion of the first hub portion to melt and fuse with the second hub portion, the radially-extending structures abutting the exterior surface of the wall of the cap and extending outwardly across the wall to form a contiguous structure of the second hub portion, the wall, and the first hub portion in a direction parallel to the aligned needle-receiving channels of the first and second hub portions.

12. A method of forming a needle and hub assembly for automatic injectors, the method comprising:

forming a first hub portion having a forward section and a flange section, the forward section defining a needle-receiving channel having a stop formed therein to limit the insertion depth of a needle inserted therein;

inserting a needle in the needle-receiving channel until the needle abuts the stop;

forming a cap having an engaging portion and a needle supporting portion, the engaging portion configured to engage a medicament cartridge of an automatic injector, the needle-supporting portion having a wall that includes an opening therein, the wall defining interior and exterior surfaces opposite each other;

arranging the cap over the needle and the first hub portion such that:

the needle and the forward section of the first hub portion extend through the opening in the wall of the cap, and the flange section of the first hub portion extends along and abuts the interior surface of the wall of the cap; and forming a second hub portion over the needle and first hub portion, the second hub portion having a forward tapering section and a plurality of radially-extending structures, the forward tapering section defining a needle-receiving channel in alignment with the needle-receiving channel of the first hub portion, the forward tapering section of the second hub portion engaging the forward section of the first hub portion, and the radially-extending structures abutting the exterior surface of the wall of the cap and extending outwardly across the wall.

13. A method of assembling an automatic injector comprising:

providing an outer housing of the automatic injector;

providing an actuation assembly in the outer housing;

filling a medicament cartridge with one or more medicament components, the medicament cartridge having an open end;

attaching the needle and hub assembly formed by the method of claim 12 over the open end of the medicament cartridge; and inserting the medicament cartridge with attached needle and hub assembly in the outer housing, the medicament cartridge in communication with the actuation assembly.

14. The method of claim 12 wherein forming the cap comprises forming the cap with a plastic material having sufficient rigidity.

15. The method of claim 12 wherein forming the first hub portion comprises forming a first hub portion having a rearward section defining a chamber in communication with the needle-receiving channel of the first hub portion.

16. The method of claim 15 further comprising covering a rearward opening of the chamber with a filter.

17. The method of claim 12 wherein forming the second hub portion having a forward tapering section defining a needle-receiving channel comprises forming a second hub portion having a forward tapering section defining a needle-receiving channel that is longer than the needle-receiving channel of the first hub portion.

18. The method of claim 12 wherein forming the first hub portion and the second hub portion comprises forming the first and second hub portions with the same material.

19. The method of claim 12, further comprising after arranging the cap and before forming the second hub portion, moving the assembly of the needle, first hub portion, and cap to a second mold having cavities defining the second hub portion.

20. The method of claim 12 wherein forming the second hub portion comprises forming the second hub portion such that a portion of the first hub portion melts to create a melt zone at which the second hub portion and the first hub portion form a single piece.

* * * * *